(12) United States Patent
Sun et al.

(10) Patent No.: US 8,384,025 B2
(45) Date of Patent: Feb. 26, 2013

(54) DEVICE FOR SEPARATING, ENRICHING AND DETECTING IONS

(75) Inventors: Wenjian Sun, Shanghai (CN); Li Ding, Manchester (GB)

(73) Assignee: Shimadzu Research Laboratory (Shanghai) Co. Ltd, Shanghai (CN)

( * ) Notice: Subject to any disclaimer, the term of this patent is extended or adjusted under 35 U.S.C. 154(b) by 144 days.

(21) Appl. No.: 13/130,254

(22) PCT Filed: Nov. 26, 2009

(86) PCT No.: PCT/CN2009/075141
§ 371 (c)(1),
(2), (4) Date: May 19, 2011

(87) PCT Pub. No.: WO2010/060380
PCT Pub. Date: Jun. 3, 2010

(65) Prior Publication Data
US 2011/0220790 A1    Sep. 15, 2011

(30) Foreign Application Priority Data
Nov. 26, 2008   (CN) .......................... 2008 1 0203393

(51) Int. Cl.
*H01J 49/26* (2006.01)
*H01J 49/42* (2006.01)
*H01J 49/10* (2006.01)

(52) U.S. Cl. ........ 250/288; 250/286; 250/287; 250/281; 250/423 R

(58) Field of Classification Search .................. 250/288, 250/286, 287, 281, 423 R
See application file for complete search history.

(56) References Cited

U.S. PATENT DOCUMENTS

| 5,491,337 A | 2/1996 | Jenkins et al. |
| 6,345,545 B1 | 2/2002 | Linker et al. |

(Continued)

FOREIGN PATENT DOCUMENTS

| CN | 1758057 A | 4/2006 |
| EP | 1678738 A2 | 7/2006 |

(Continued)

OTHER PUBLICATIONS

H. Tammet, The Limits of Air Ion Mobility Resolution, Aerosol Sci., 1998, p. S63-S64, vol. 29.

(Continued)

*Primary Examiner* — Nikita Wells
(74) *Attorney, Agent, or Firm* — Morris Manning & Martin LLP; Tim Tingkang Xia, Esq.

(57) ABSTRACT

A device for separating, enriching and detecting ions comprises: a gas tube, in which a carrier gas flows at a uniform rate; an ion source; multiple electrodes provided in the gas tube and applied with electric voltages respectively, so that at least an electric field is produced along the axis of the gas tube; an ion detector; and an ion extraction channel, by which specific enriched ions will be guided across the side wall of the gas tube toward the ion detector and be analyzed. The device enriches ions utilizing the following characteristic: compound ions with specific ion mobility maintain a dynamic balance for a period of time in a flow field under the combination of a carrier gas and a suitable electrical field against the direction of the carrier gas. Simultaneously, multiple compound particles with different ion motilities can be separated and enriched at positions with different electrical field intensities in a flow field in the same manner. The device also comprises synchronously export latitudinally enriched ions at different positions in a flow field, and performs later mass analysis using a mass spectrometer.

17 Claims, 8 Drawing Sheets

U.S. PATENT DOCUMENTS

| | | | |
|---|---|---|---|
| 7,199,362 B2 * | 4/2007 | Rockwood et al. | 250/286 |
| 7,368,709 B2 | 5/2008 | Guevremont et al. | |
| 7,547,878 B2 * | 6/2009 | Schultz et al. | 250/282 |
| 7,911,146 B2 * | 3/2011 | Dunn-Rankin et al. | 315/111.91 |
| 8,129,675 B2 * | 3/2012 | Schultz et al. | 250/282 |
| 2003/0213903 A1 | 11/2003 | Ichimura et al. | |

FOREIGN PATENT DOCUMENTS

| | | |
|---|---|---|
| WO | 2005045876 A2 | 5/2005 |
| WO | 2005104182 A | 11/2005 |

OTHER PUBLICATIONS

Ignacio G. Loscertales, Drift Differential Mobility Analyzer, J. Aerosol Sci., 1998, p. 1117-1139, vol. 29, No. 9.

Victor V. Laiko, Orthogonal Extraction Ion Mobility Spectrometry, J. Am. Soc. Mass Spectrom, 2006, p. 500-507, vol. 17.

Richard C. Flagan, Opposed Migration Aerosol Classifier (OMAC), Aerosol Sci. and Technol., 2004, p. 890-899, vol. 38.

* cited by examiner $V_1 = U_1$
$V_2 = U_2 + V\cos(\Omega t)$
$V_3 = U_3 - V\cos(\Omega t)$
$V_4 = U_4 + V\cos(\Omega t)$
$V_5 = U_5$

DEVICE FOR SEPARATING, ENRICHING AND DETECTING IONS

FIELD OF THE INVENTION

The invention relates to enrichment and detection of chemicals, and more particularly, to a device for separating, enriching and detecting ions.

BACKGROUND OF THE INVENTION

Fast, accurate and sensitive detection equipment is highly demanded in dealing with the increasing problem of worldwide smuggling, drug trafficking and acting of terrorism. At present, the ion mobility spectrometer with its lightweight, fast, and sensitive performance has been widely used in public security checking points such as in the airport and sport stadium. Ion mobility spectrometry is a relatively new gas separation and detection methods. Different from the gas chromatography, the compounds to be separated and detected in the ion mobility spectrometer must be ionized, and then under the effect of the electric field in accordance with the molecular size of the ion to be separated.

In principle, there are two categories of ion mobility spectrometers may be used in various security agencies. The first category is the traditional ion mobility spectrometer (IMS). In IMS, the operation mechanism involves application of a dc axial electric field in a tube filled with neutral gas, where ions are accelerated by the electric field and collided with neutral gas and reaches its velocity which is proportional to the field strength (v=KE).

Here v is the velocity of ion, E is electric field strength, K the ion mobility which is inversely proportional to the ion's cross-sectional, thus is a measure of ion size. The Differential Mobility Spectrometer (DMS), as the second category, makes use of the difference of ion mobility between in the high field and low field, to achieve the separation of ions. The principle is as follows: ions enter the gap between a pair of parallel electrodes and travelling along with a gas flow. One of the electrodes is applied with an asymmetrical RF waveform including a short period $t_H$ of high field $E_H$ and a longer period $t_L$ of opposite low field $E_L$. The net drift of ion after the high and low field period is zero, that is $K_H E_H t_H + K_L E_L t_L = 0$, where $K_H$ and $K_L$ are the ion mobility and are assumed equal. However, it is common that ion mobility changes from a low field condition to the high field condition. This results in the net transverse displacement being non-zero. A compensation DC voltage, which is normally applied on another parallel electrode, is used to cancel the displacement, to ensure that the ions can flow through the gap between electrodes and be detected at the exit. Since difference of ion mobility in high and low field is changed from ion to ion, the required compensation voltage is changed with ions, so these different compensation voltages can be used to distinguish different ions. FAIMS, the high field asymmetric ion mobility spectrometry is just one variation of DMS and shared the same principle of operation while its electrodes use the concentric cylindrical geometry. Compared to the mass spectrometer, the resolution of the ion mobility spectrometer is relatively lower. However, because it can operate in low vacuum or even atmospheric pressure condition, thereby reduces the cost of vacuum system, the ion mobility instrument gains advantage for being made into a relatively compact instrument for quick on-site testing.

A widely used sampling method for IMS by security departments is to use paper swab to get small amount of substance from the surface to be sampled and desorb the substance from the swab in the ion source of IMS. The current limit of detection of this method is usually ng to pg levels. However, the limitations of this method is the need to have someone perform the sample collection from targeted mater or persons, and a localized sampling can not cover all of the measured object, so easy to miss the contaminated part.

To solve this problem, another security equipment with ion mobility spectrometry has been developed where the mater to be checked need to enter an air shower compartment and part of drained air is lead to the ion mobility instrument. In this method, trace amount of brush out substance is mixed with large amount of environment air, so the concentration of the sample would be much diluted thus even higher sensitivity of the detection is required. In order to further improve the instrument sensitivity, pre-concentration of sample before test is proposed. As described in U.S. Pat. No. 6,345,545, the sample particles that flow into the detector are absorbed by a series of absorbing meshes. After a period of time for absorbing, the sample is subjected a strobe of heat making online desorption from adsorbates and the gas phase of sample is introduced to the next level of detecting system. Such enrichment method has been implemented in Syagen's "Guardian Portal". However, within this approach, there are still large number of analyte can not be absorbed and the adsorption and desorption requires a relatively long time.

Ions produced by continuous ion source may be condensed on their way leading to the detector by employing a region where the axial electric field is minimized, and a subsequential pulsed extraction may be used for sending them to the detection system. These devices have been disclosed by Anthony Jenkins as an "ion-enrich region" in U.S. Pat. No. 5,491,337, and by Richard Smith as an hourglass ion funnel described in European patent EP1678738. However, such ion enrichment devices did not separate or select the ion to be enriched, therefore it is non-selective enrichment. Above methods are neither meant to be working in high flow condition as the high flow velocity might cause instability of ion in the enrichment region, so the sample throughput is limited.

However, if ions are driven by the electric field and by the gas flow in an opposite way at the same time and two forces applied to the ions balance each other while more ions are keep coming, this species of ion can be concentrated. The concept of the balance dated back in 1898 and is proposed and implemented by Zeleny (J. Zeleny, Philos, Mag., 1898, 46, 120-154). However, the purpose of the experiment in that time is to measure the speed ratio of two ions under the application of the electric field, so no ion enrichment is detected. Later, Loscertales (J. Aerosol Sci. 1998, 29, 1117-1139.), and Tammet (Aerosol Sci. 1998, 29, S63-S64.), brought the idea of balance between electric field and flow to the differential mobility analyzer (DMA), in which a superimposed axial electric field is used to cause stagnation of ion's axial motion by the influence of flow as well as the axial field, so the ion can only move towards detector. This method only improved the resolution of DMA, but no enrichment can be achieved since the retention time in the drifting tube is very limited as the result of existence of axial field component.

Flagan (Aerosol Sci. Technol. 2004, 38, 890-899.) and Rockwood (U.S. Pat. No. 7,199,362), also used this balance mechanism in a series of ion mobility spectrometer. Different from instruments mentioned above, Flagan and Rockwood, used the air flow rather than electric field in a direction perpendicular to the balanced forces, so their method is called cross-flow ion mobility spectrometry. Similar to Loscertale and Tammet, this method didn't achieve the enrichment of the ion even though the balance of flow and electric field is satisfied, because again there exists the radial force.

Satoshi Ichimura and colleagues proposed another way of using gas flow and axial electric field for ion enrichment which is disclosed in U.S. publication No. 2003/0213903. In this method, the analyte ions going against the constant gas flow in the drift tube with diameter gradually reduced, while the electric field causing ion drift in axial direction is constant. As the diameter decreases, the ions are subjected to the increased reverse flow velocity. An ion with certain ion mobility can be stopped in a place where the ion drifting velocity caused by the electric field and flow velocity equals. As this kind of ions having net velocity approaches to zero, the continuous arrival ion can be enriched in this place. This method has the advantage of not only that the analyte can be enriched and detected, but also can filter out the small molecular ions generated in atmospheric ionization source (with greater mobility) using a weak exclusion electric field (for example in the negative mode, exclusion of oxygen ions), thereby reducing the space charge effect on ion concentration and detection. However, the way relying on changes in diameter to change the gas axial velocity ignored the gas radial velocity changes, the radial velocity component of the ion causes rapid movement to the wall, so that the ion concentration becomes very difficult. The Laiko in his article (J. Am. Soc. Mass Sepctrom. 2006, 17, 500-507) simulated the case in a similar instrument, in which ion motion affected by the flow in radial direction is just used to eject ion through the side wall of drift tube. This gives an evidence of difficulty in the enrichment method proposed by Ichimura's patent.

In another U.S. Pat. No. 7,368,709, Roger Guevremont describes the use of uniform flow, and the gradient of the axial electric field to separate ions with different ion mobility. However, this method can only be able to collect the ion group that is selected by one of the compensation voltage (CV) of the DMS. In another word, all survived and enriched ions must have single differential mobility. Large amount of useful and informative ions will be lost. Another limitation of this method is that ions concentrated in the tube are finally detected by removing them out of the tube in the axial direction, so the ions that have been already separated according to their mobility may be diffused again in the process of detection, thus the resolution of separation is deteriorated. Also, the introduction of ions from the ion source should be suspended during the detection period, therefore reduces the operation efficiency.

SUMMARY OF THE INVENTION

The present invention is to solve the technical problem for providing an ion separation, enrichment and detection device for fast and efficient ion detection.

An apparatus is proposed in the present invention for ion separation, enrichment, and detection. It contains: a gas tube, an ion source, multiple electrodes, an ion extraction channel, and an ion detector. The gas tube is operated under ambient pressure or low vacuum within which there is a gas flow with constant velocity. At least one type of ions generated by the ion source enters the gas tube. Multiple electrodes are placed inside the gas tube, and different voltages are applied onto different electrodes. In such case at least one electric field is established in the gas tube. When the ions flow along with the gas flow, they will experience an electric field against their flow direction. In such case ions with a specific mobility can be accumulated in the gas tube due to the balance of the drift velocities caused by flow field and electric field. An ion extraction channel is used to connect ion enrichment region with the ion detector. Therefore, the ions with a specific mobility can be accumulated and then introduced into the ion detector from the side of the gas tube.

In this apparatus, the ions moved with the gas flow with a constant velocity along the axis of the gas tube. In the mean time, the ions experienced an electric field against the gas flow. When the gas flow caused ion velocity equals the electric field caused ion velocity, the net velocity of the ions is zero. By then the ions will be enriched on the balanced location and the total enrichment time will only be limited by ion diffusion.

In one of the embodiments of this invention, there is one electric field in the gas tube and the electric field is uniform along the tube axis.

In one of the embodiments of this invention, the voltages on the multiple electrodes varied with time, so that the axial electric field along the tube varied with time. Under this condition ions with different mobility can be enriched at different time in the same location, and therefore the sensitivity of the instrument can be enhanced.

In one of the embodiments of this invention, the ions would pass through a gradient electric field before they entered the electric field to be enriched. The strong side of the gradient electric field has the same field strength as the electric field for enrichment, and the electric field of the gradient electric field gradually decreases along the direction of the counter gas flow. The existence of this gradient electric field can keep those ions with large mobility (mobility larger than that of the ions to be enriched) away from the electric field for ion enrichment, and to move them upstream before quenching them on the wall of the gas tube.

In one of the embodiments of this invention, multiple electric fields can be generated in multiple segments of the gas tube among which each electric field is uniform within the segment and is increased across different segments. In such way ions with different mobility can be accumulated in different segments. In another embodiment of this invention, a gradient electric field is generated with multiple electrodes in one segment of the gas tube, and this gradient electric field is increased along the direction of the gas flow. In the embodiments mentioned above, the ions are moved in the gas tube with the gas flow with a constant velocity and experienced counter force from the electric fields established within the gas tube. The electric field is different at the different locations of the gas tube and it is increased along the direction of the gas flow. Therefore, when a mixture of analyte ions enters the gas tube with a constant velocity, ions with different mobility will be enriched in different regions of the gas tube according to their respective mobility. Therefore, separation of ions in space can be realized.

In one embodiment of the invention, the voltages applied on the multiple electrodes contain radial component pointing towards the central axis of the gas tube.

In one embodiment of the invention, the multiple electrodes include multiple mesh electrodes covering the cross section of the gas tube, between which different electric field can be formed for enriching ions with different mobility.

In one embodiment of the invention, the multiple mesh electrodes are composed of multiple curved surface mesh electrodes and the concave surface of the mesh electrode faces the direction of the gas flow.

In one embodiment of the invention, the adjacent ones of the multiple electrodes are applied RF voltages of different phase to produce a radial focusing electric field, and the averaged force experienced by the ions from this electric field points towards the central axis of the gas tube.

In one embodiment of the invention, the multiple mesh electrodes are composed of multiple curved surface mesh electrodes and the convex surface of the mesh electrode faces the direction of the gas flow.

In one embodiment of the invention, the multiple electrodes are ring shaped electrode array which surrounds the gas tube, and different voltages are applied on the different electrodes of the ring shaped electrode array in order to form an electric field along the axis of the gas flow.

In one embodiment of the invention, the ion extraction channel connects to the aperture located on the wall of the gas tube so that the enriched ions in the gas tube can exit the gas tube from the respective regions with the corresponding electric field.

In one embodiment of the invention, the ion extraction channel is stretched from the side of the gas tube into the center of the gas tube so that the enriched ions in the gas tube can exit the gas tube from the center of the respective regions with the corresponding electric field.

In one embodiment of the invention, the ion detector connected to the ion extraction channel is a Faraday cup detector array.

In one embodiment of the invention, the ion detector connected to the ion extraction channel is an ion trap array mass analyzer.

In the present invention, by increasing the radial electric field one can further increase the ion enrichment time. On the other hand, the invention provides the method for enriching different ions at different times or in multiple regions at the same time. Furthermore, since the axial electric field distribution along the gas tube can be changed by changing voltages applied on the different electrodes, the spacing between different enrichment regions can also adjusted, which makes it possible to mount multiple ion extraction channels in fixed positions along the gas tube. Since each ion trap in the ion trap array corresponds to an enrichment region, the ion groups in various regions can be extracted radially at the same time, and be captured and detected by the corresponding ion trap, which greatly enhance the detection efficiency while maintaining the spatial resolution of the device.

BRIEF DESCRIPTION OF THE DRAWINGS

The accompanying drawings illustrate one or more embodiments of the invention and, together with the written description, serve to explain the principles of the invention.

DETAILED DESCRIPTION OF THE INVENTION

This invention involves sample enrichment, separation, and detection after ionization in the gas phase. The invention is especially advantageous for detecting trace amount of substance such as explosives and illicit drugs concerned by public security department.

Figure 1:
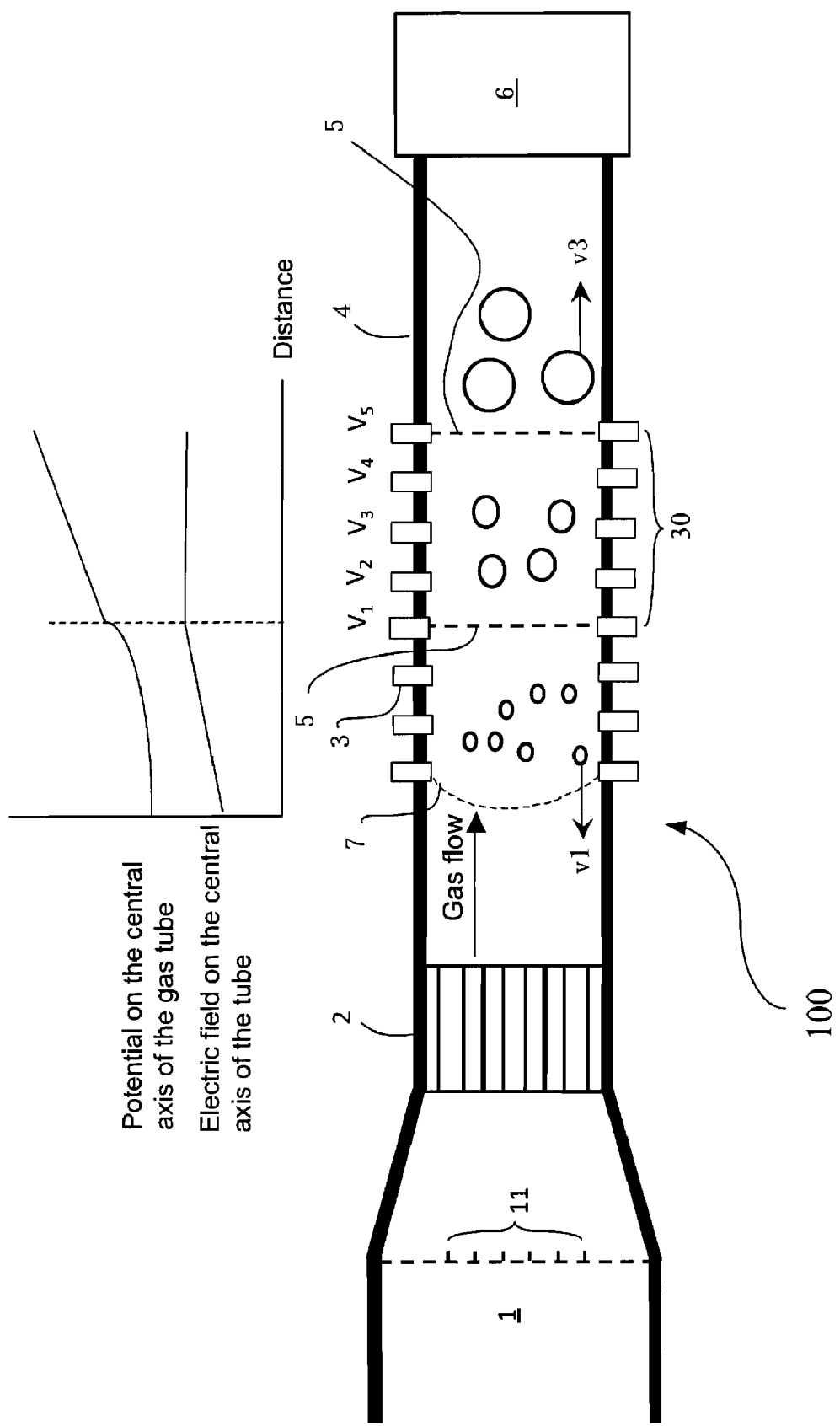
FIG. 1 shows schematically a device for ion enrichment and the basic principle of the ion enrichment according to one embodiment of the present invention.

As shown in FIG. 1, the gas containing analytes enters the ion enrichment device from the left side of device 100 of the gas tube 4. The gas containing analytes will go through a continuous ion source before entering the gas tube 4. In order to rapidly ionize the trace amount of analyte in the gas flow, the ion source 1 can be an array of corona or glow discharge ion source with discharge needle array. Compared with the single needle discharge source used in normal ion source, the present design has better ionization efficiency with multiple discharge needles 11 located on different positions of the cross section of the gas tube 4. For such an ion source, one can change the polarity of the voltage applied on the needle to change the polarity of the ion source. When positive voltage is applied on the discharge electrodes, positive ions will be generated and thus the ion enrichment device is operated in positive ion mode; and when negative voltage is applied on the discharge electrodes, negative ions will be generated and thus the ion enrichment device is operated in negative ion mode. Of course, the polarity of some other electrode components of the device need also be switched for adapting different polarity modes. Moreover, other ionization method can also be applied to the present device, such as a photoionization source which has high selectivity.

In order to enrich ions in the gas flow tube 4 before the thermal diffusion of the ions drive the ions to the wall of the gas tube 4, the reverse gas flow velocity and ion drift velocity driven by the electric field should be relatively high. This would require a relatively high ionization rate for the ions source. The ion source or combination of them described above has achieved this goal which is ionizing as many neutrals as possible when they passed through the ion source region with large velocity.

The enrichment process is achieved by balancing the gas flow velocity and ion drift velocity driven by the electric field. Thus, it becomes very important to maintain a uniform gas flow velocity and direction in every region of the gas tube 4. In FIG. 1 the drift direction of the ions driven by the electric field is from right to left, and thus the direction of the gas flow has to be from left to right and it should not contain radial velocity component. The basic flow type for achieving such condition is the laminar flow in which the flow direction of the gas molecules is macroscopically parallel to the wall of the gas tube and the flow does not contain turbulence. Therefore, a laminar flow converter is installed at the entrance of the gas tube 4. In addition, in order to make the gas flow velocity in the gas tube more uniform, the inlet and outlet of the gas tube can also use the classic wind tunnel design.

In the gas tube 4 an electric field region 30 is formed with a pair of mesh electrodes 5 and multiple ring electrodes 3. The voltages applied to the electrodes from left to right along the direction of flow gradually increases linearly, and thus within the range a uniform electric field strength is maintained as shown in the upper part of FIG. 1. When the ions in the laminar flow passed through this electric field region 30, their net velocity in the axial direction is zero if the rate of migration under the electric field is just equal to the gas flow velocity, ($v_2 = K_2 E = -v_{flow}$), among which K is the mobility constant, E is the electric field, $v_{flow}$ is the gas flow velocity. Thus such ions can be enriched in the area (also known as ion enrichment region). For ions with larger mobility ($K_1 > K_2$), its velocity induced by electric field will be greater than the gas flow velocity ($v_1 = K_1 E > -v_{flow}$), then these ions will be expelled from the field from right to left. On the other hand, for ions with smaller mobility ($K_3 < K_2$), its drift velocity induced by the electric field will be smaller than the gas flow velocity ($v_3 = K_3 E < -v_{flow}$), then these ions will pass the electric field region from left to right, and eventually exit the system from the exhaust fan 6. It should be noted that if there is no electric field on the left side of the ion enrichment region 30, ions expelled from the left side of the enrichment region ($v_1 = K_1 E > -v_{flow}$) will be brought back to the vicinity of the left mesh electrode 5 near the ion enrichment region 5, and possibly be extracted towards detector along with the target ions, causing a degradation of the instrument resolution. To avoid such situation, one can add an electric field gradient on the left side of the ion enrichment region 30 and the field strength on the right side of the field gradient is equal to that of the ion enrichment region and gradually decreases towards left. With the existence of this field gradient, the expelled ions from the ion enrichment region will move upstream continuously and eventually leave the ion enrichment region. As shown in FIG. 1, this field gradient can be formed with a curved mesh electrode 7 (concave side facing the gas flow) and a planar mesh electrode 5 located on the right and left side of the ion enrichment region 30, respectively, and its field strength would gradually decrease from right to left as shown in the upper part of FIG. 1. At the same time, this type of curved mesh electrode has the defocusing effect for ions in the radial direction, thus ions expelled from the ion enrichment region 30 will eventually splatted on the wall of the gas tube 4.

From the above, the gas tube 4 could selectively enrich ions with a specific mobility, and the degree of its enrichment will increase along with enrichment time. However, the maximum time for efficient enrichment is limited by the diffusion time of ions from inside to the wall of the gas tube 4. This is to say that although the net axial velocity of the ions caused by gas flow and electric field is zero, the ions will still gradually died out on the wall of the gas tube 4 due to thermal diffusion. At that point the ion concentration cannot be increased anymore.

Figure 2:
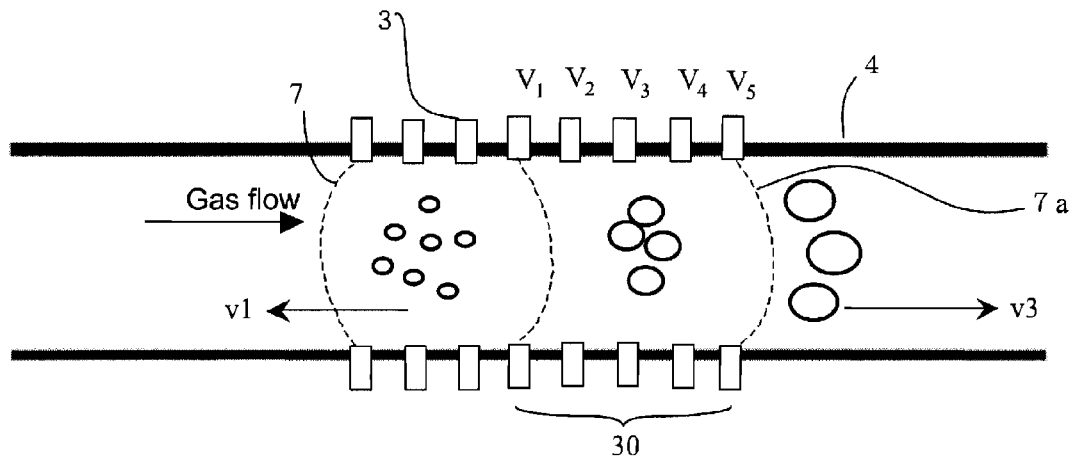
FIG. 2 shows schematically a structure of the curved surface mesh electrodes with its concave surface facing the direction of the gas flow in the ion enrichment device, and also the focusing effect of the electric fields according to one embodiment of the present invention.

In order to extend the ion enrichment time, in one embodiment, one can use a curved mesh electrode 7a to replace the flat mesh electrode 5 to introduce radial component of the electric force pointing toward the axis of the gas tube 4 so that ions can be focused in the radial direction. FIG. 2 shows the mesh electrode design in the gas tube 4 in one embodiment of the present invention. As shown in FIG. 2, the mesh electrode 7a has its convex surface facing the gas flow, and axial component of the electric force provide the ion drift velocity to balance the gas flow. In addition, the radial component of the electric force is the focusing field for ions, and it decreases from the wall to the central axis of the gas tube. In such case, the ion diffusion in the radial direction can be efficiently suppressed.

In another embodiment, the extension of the ion enrichment time can also be realized by applying RF voltages on the ring electrodes 3 forming the electric field in the gas tube 4. For example, one can apply two RF voltages with the same amplitude but opposite phase on the adjacent ring electrodes as illustrated in FIG. 1. When ions approached the vicinity of the wall of the gas tube 4, the electric field generated by the two RF voltages will drive the ions towards the central axis of the gas tube 4, and thus reduce the loss of ions on the wall and increase the enrichment time.

When using the curved mesh electrodes 7a, a quadrupole field will be formed between the two curved mesh electrodes. Although the radial component of the electric force would defocus ions for the situation where the concave surface of the mesh electrode faces the gas flow, the radial diffusion can be controlled well by the RF field described above. With the superposition of the DC and RF electric field, the ion enrichment time can be greatly increased.

Figure 3:
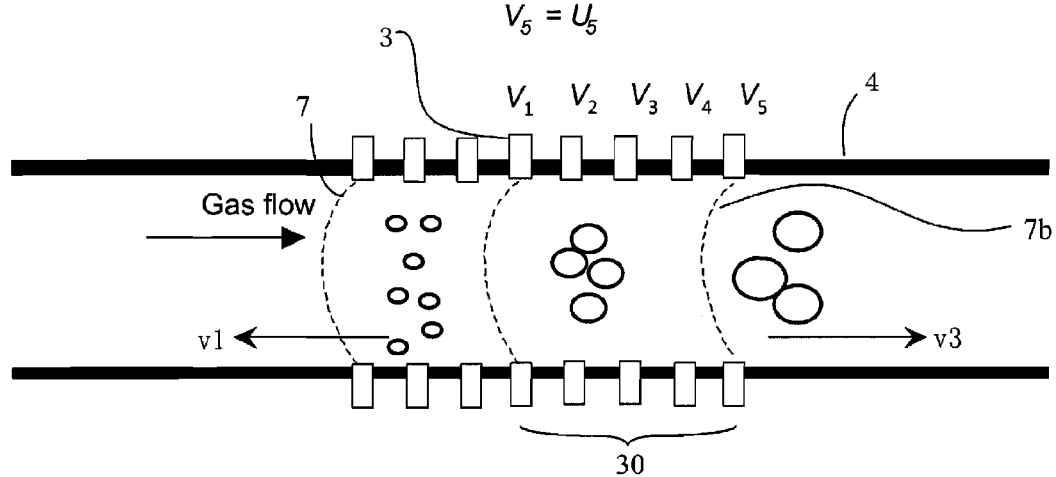
FIG. 3 shows schematically a structure of the curved surface mesh electrodes with its convex surface facing the direction of the gas flow in the ion enrichment device, and the focusing effect caused by the DC voltage applied on the curved mesh electrode and the RF voltages applied on the ring electrodes according to one embodiment of the present invention.

In the devices shown in FIG. 2 and FIG. 3, there is also need for expelling and keeping away ions from the left side of the ion enrichment region. The solution to this issue the same as the one shown in FIG. 1, namely adding a field gradient to the left side of the ion enrichment region so that the expelled ions will move upstream and eventually splat on the wall of the gas tube.

For the device shown in FIG. 1, it only has one electric field thus it is more suitable for enriching a certain interested compound. The enrichment of other compounds can be realized by adjusting the field strength of the electric field. However, the ions continuously generated in the ion source cannot be fully utilized in this case if the field strength is changed periodically. This is because only ions with a specific mobility can be enriched at a time and ions with other mobility will be lost. Therefore, the device shown in FIG. 1 is more suitable for enriching and detecting single component analyte.

Figure 4:
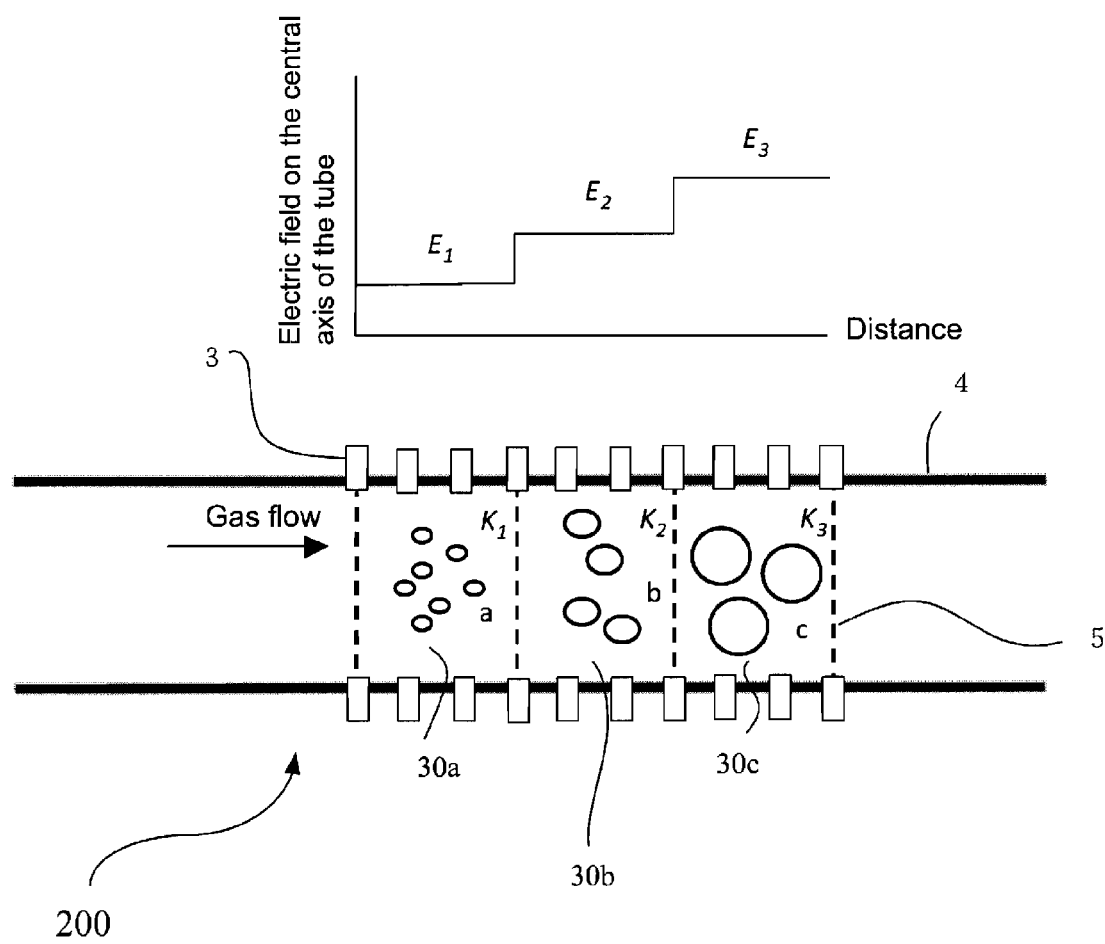
FIG. 4 shows schematically the basic principle for enriching ions with different mobility in uniform electric field at different locations of an ion enrichment device.

However, in the situation where multi-component analyte need be enriched, one can modify the device shown in FIG. 1. The structure of the modified part for the device is shown in FIG. 4 and other parts of the device are the same as those shown in FIG. 1. In the ion enrichment device 200 shown in FIG. 4, the gas tube 4 is partitioned by mesh electrode 5 into multiple electric fields along the axial direction. The electric field is uniform within each partitioned electric field, and it increases from left to right for different partitioned field in the gas tube 4 as shown in FIG. 4 for $E_1$, $E_2$, and $E_3$. In this situation we assume the mixed analyte contains three components and each component has its own specific mobility ($K_1$, $K_2$, and $K_3$), and $K_1 > K_2 > K_3$. The separation and enrichment mode in the gas tube 4 are discussed as below. When this mixture of ions to be analyzed enter the gas tube 4 from the left side, the ions will encounter the electric field $E_1$. $E_1$ can be adjusted to an appropriate value so that ions with highest mobility ($K_1$) can obtain enough counter velocity from the electric field to balance the gas flow velocity, i.e. $v_1 = K_1 E_1 = -v_{flow}$. At this point other two types of ions (b and c) have lower counter velocity (caused by electric field) than that of the gas flow, i.e. $K_2 E_1 < K_1 E_1 = -v_{flow}$ and $K_3 E_1 < K_1 E_1 = -v_{flow}$. Therefore, b and c ions will pass the first electric field (ion enrichment region 30a) and continuously travel into the second electric field region (ion enrichment region 30b) from left to right along the gas tube. The field strength in the second electric field is set to be higher than that of the first one, and also $v_2=K_2E_2=-V_{flow}$. Therefore, b ions with mobility $K_2$ will be enriched here. For the c ions with mobility $K_3$, the ion drift velocity is still less than the velocity of the gas flow, i.e. $K_3E_2<K_2E_2=-v_{flow}$, and thus c ions will pass the second region and be enriched in the third electric field region (ion enrichment region 30c), where $v_3=K_3E_3=-v_{flow}$.

Figure 5:
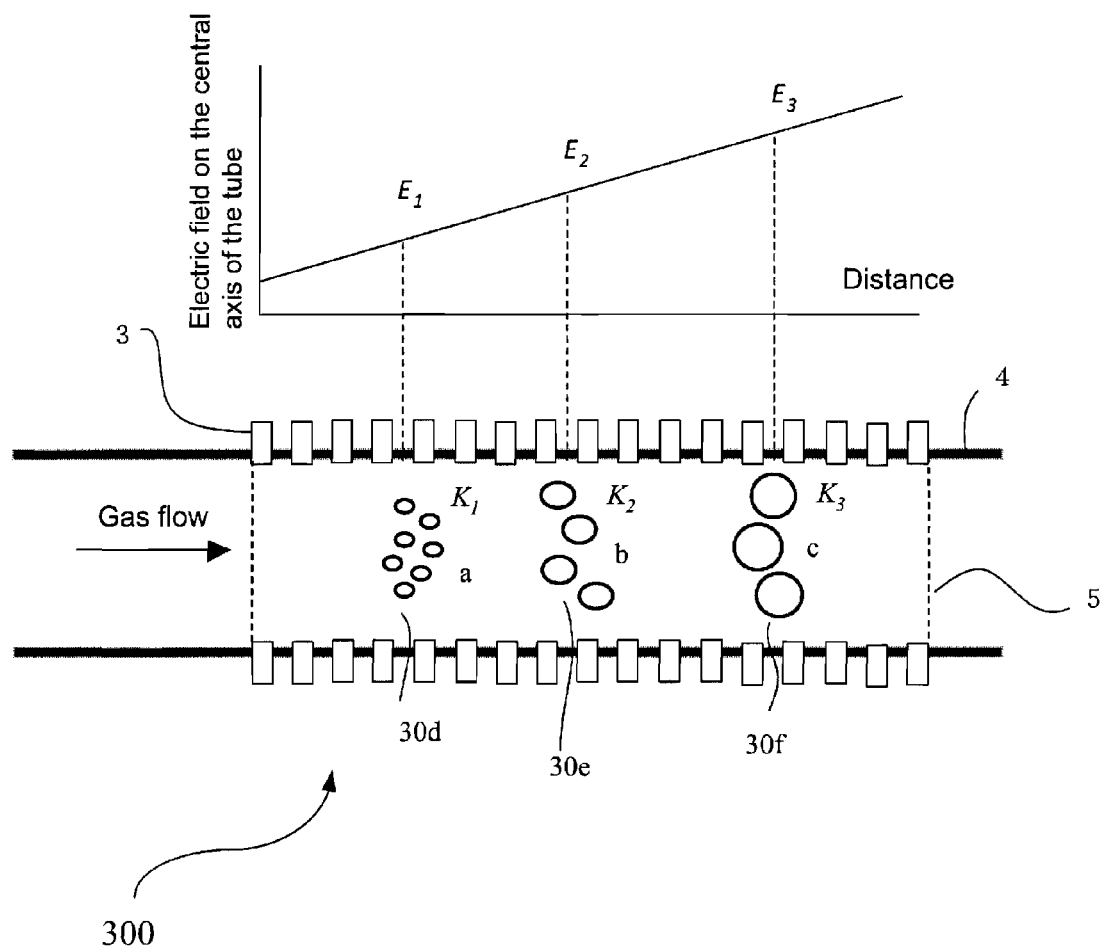
FIG. 5 shows schematically the basic principle for enriching ions with different mobility in gradient electric field at different locations of an ion enrichment device according to one embodiment of the present invention.

Enrichment of ions described above can also be achieved by using gradient electric field as discussed below. In the device 300 as shown in FIG. 5, ion mixture (a, b, and c) would enter the gas tube 4 from the left, and flow through the electric field region from left to right. Different from the device shown in FIG. 4, the device shown in FIG. 5 has a gradually increasing electric field from left to right in the gas tube 4 instead of uniform field. Indicated by the diagram at the upper part of the FIG. 5 for the relationship between the electrode voltage and electrode position, this linear increase of the electric field can be achieved by applying appropriate voltages on the ring electrodes 3 to meet the relationship of $E=dU/dx \propto 2x$ (from $U \propto x^2$, x is the position in the gas tube 4). When ion mixture a, b, and c with mobility $K_1$, $K_2$, and $K_3$, respectively, flows through the gas tube 4, the counter velocity acquired from the electric field by any type of the ions will gradually increase. When the electric field is strong enough at certain point, say $E_1$, ions with largest mobility, namely a ions, will obtain enough counter velocity to balance the gas flow, i.e. $v_1=K_1E_1=-v_{flow}$, and thus to be enriched here. At this point, other two types of ions b and c still have lower counter velocity than that of the gas flow, thus they would continuously travel downstream until they obtain enough counter velocity for each to balance that of the gas flow. Therefore, three ion enrichment regions can be formed (30d, 30e, and 30f).

When using the device shown in FIG. 5, the existence of the quadrupole field induced by the axial gradient field would cause defocusing of ions in the radial direction. Similar to the principle shown in FIG. 3, this defocusing effect can be suppressed by applying RF voltages on the ring electrodes.

The field strength in the device shown in FIG. 5 is continuously changed, thus theoretically ions with the same mobility can only be enriched on a certain plane which corresponds to a certain field strength. Although factors such as ion initial velocity, ion diffusion, and electric field defects would weaken this axial focusing effect, the spatial resolution is still higher than that of the device shown in FIG. 4. Note that although the electric field increases linearly along the axial direction of the gas tube 4, the mobility K of different analyte components does not change linearly, which makes it difficult to obtain an evenly distributed enrichment regions along the axial direction of the gas tube 4. In one embodiment of the current invention, this limitation can be levitated by combining the principles demonstrated in FIG. 3 and FIG. 5, namely applying gradient field in each partition of the gas tube 4 in the device shown in FIG. 3.

After the mixture of ions is enriched in the gas tube 4 of the device shown in FIG. 4, they need to be detected by a detector to complete the entire analyzing procedure. Both U.S. publication No. 2003/0213903 and U.S. Pat. No. 7,368,709 mentioned in the Background of the present invention involve detecting ions in the axial direction at the end of a gas tube after a period of enrichment.

Figure 6:
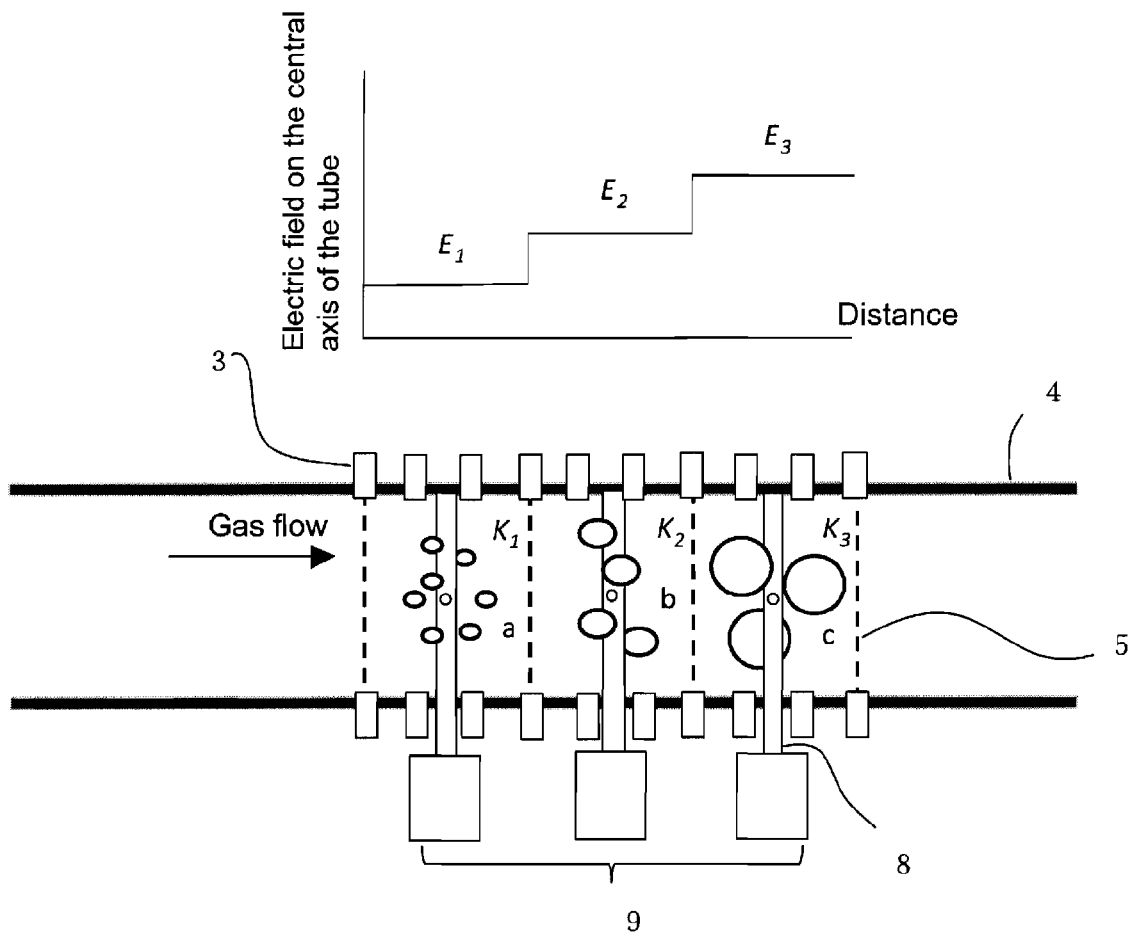
FIG. 6 shows schematically a structure for extracting the enriched ions from an aperture located at different locations on the middle part of the gas tube. The extracted ions are transferred through an ion transfer tube toward outside of the gas tube and detected by Faraday cup detectors according to one embodiment of the present invention.
Figure 7:
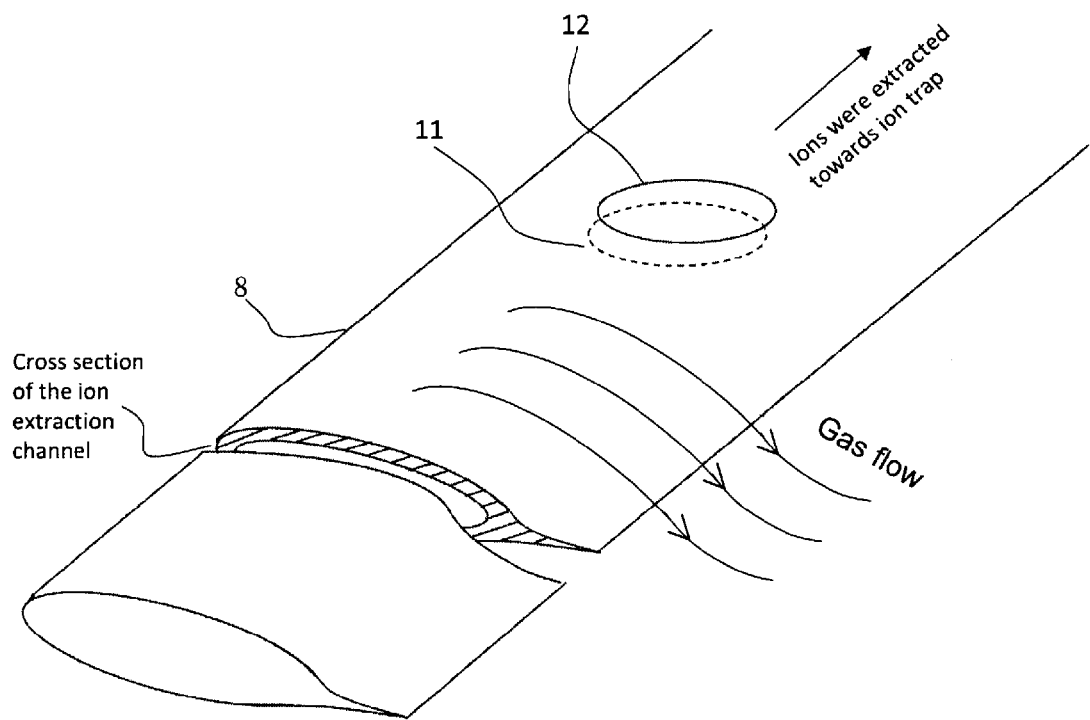
FIG. 7 shows schematically the geometrical structure of the ion transfer channel in the ion enrichment device illustrated in FIG. 6.

Considering some limitations of the axial detection such as loss of spatial resolution, the present invention adopts the ion extraction and detection method based on radial extraction of ions in the gas tube 4. FIG. 6 shows the schematics for radial extraction and detection of ions using Faraday cup detector. The device shown in FIG. 6 has the same gas tube structure as the one in FIG. 4, and each partition has uniform electric field confined by adjacent two mesh electrodes. The ion extraction channel 8 is inserted into the gas tube radially from the side wall of the gas tube. The ion extraction channel is across the entire cross section of the gas tube 4 considering the symmetry, and it is sealed well at the contacting point with the gas tube 4. In order to minimize the disturbance of the ion extraction channel to the gas flow, the ion extraction channel is designed to have a streamline structure (shown in FIG. 7). There are two apertures located on the top and bottom of the ion extraction channel, respectively (bottom aperture 11 and top aperture 12) so that ions can be rapidly extracted (the size of the ions in the FIG. 7 is exaggerated for demonstration purpose, the actual ion size should be much smaller than that of the aperture). The ion extraction channel 8 is connected to external Faraday cup detector 9 through a fast pulse valve. The purpose of doing so is to make sure that the ions will only be extracted during the time of detection in order to avoid any disturbance of the gas flow caused by the extraction process. One should note that the pressure in the Faraday cup detector region should be lower than that of the gas tube 4 so that ions can be easily extracted by the pressure difference.

Figure 8:
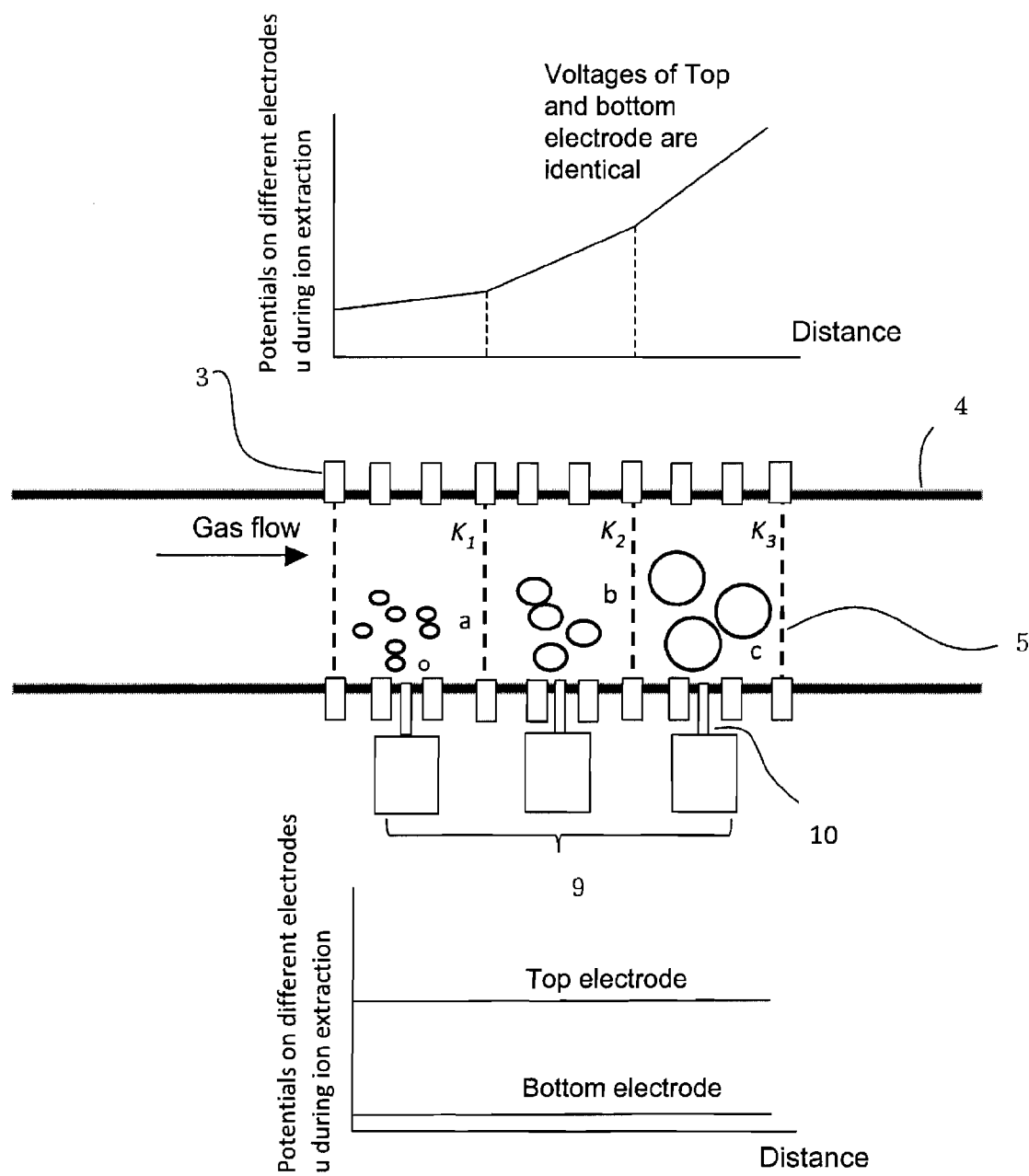
FIG. 8 shows schematically a structure having one or more ion extraction channels for extracting the enriched ions from apertures located at different locations on the wall of the gas tube under the influence of DC voltages, according to one embodiment of the present invention. The extracted ions are transferred through an ion transfer channel toward outside of the gas tube and detected by Faraday cup detectors.

In order to avoid the disturbance of the ion extraction channel 4 to the flow of gas in the gas tube 4, the gas tube 4 can also be designed to the one as shown in FIG. 8. The ion extraction channel 10 in FIG. 8 is not inserted into the gas flow tube, instead, it is connected to the aperture on the wall of the gas tube 4. In such ion extraction structure, each of the ring electrodes 3 in the gas tube is segmented to two parts (upper and lower parts). The voltages on the upper and lower parts of the ring electrode are the same during the period of enrichment, but they become different (voltage on the upper is higher than the voltage on the lower) during the period of ion extraction. At this moment, ions will be driven by the electric force towards the aperture on the wall of the gas tube 4.

Figure 9:
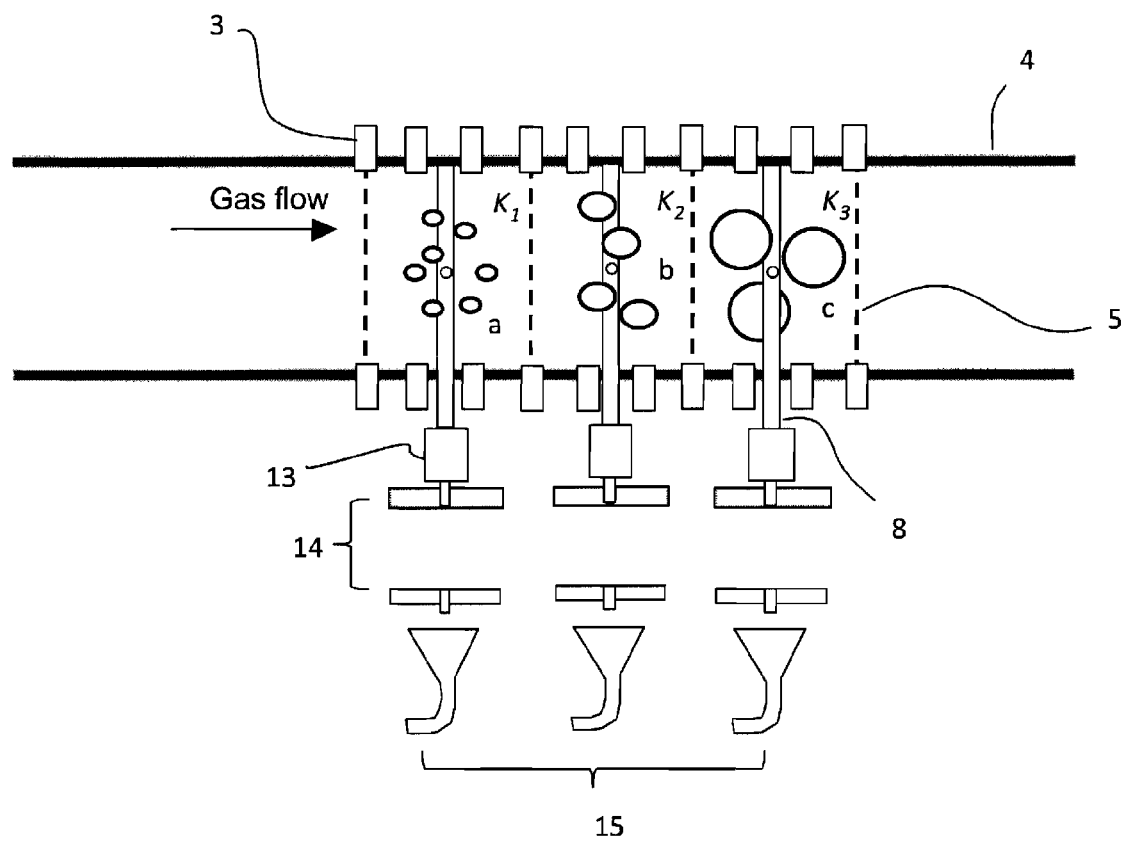
FIG. 9 shows schematically ions enriched in different locations in the ion enrichment device extracted towards outside of the gas tube and detected by a mass spectrometer array according to one embodiment of the present invention.

To further improve the resolution of the device described in the present invention, one can combine the ion enrichment device shown in FIG. 4 with a mass analyzer. This will make it possible to differentiate different compounds with similar mobility and decrease the possibility for getting false positive results. Since ions with different mobility will be enriched at the same time in the gas tube 4, the ideal detection method is to use multiple mass analyzers to analyze those ions at the same time. Different types of mass analyzers can be used for serving this purpose, but an ion trap array 14 seems a better choice, considering the limited space and relatively high pressure near the gas tube 4. Therefore, as shown in FIG. 9, an ion trap array 14 can be mounted on one side of the gas tube 4. Each ion trap in the ion trap array 14 corresponds to one ion enrichment region. All the ion traps in the array are spatially independent, but they are driven by the same voltages. Similar to the device shown in FIG. 6, a fast pulse valve 13 is also needed between the ion trap array 14 and the gas tube 4 so that the gas flow will not be disturbed during the period of enrichment. In the mean time, since the pressure in the ion trap array 14 is much lower than that in the gas tube 4, the opening period for the pulse valve need to be very short, say several ms, in order to avoid high pressure in the ion trap array 14. In addition, the ion detector in the ion trap array 14 can be an electron multiplier array 15.

The embodiments described above are only for demonstrating the possibility of the present invention. Persons with related professional knowledge should be able to easily design multiple configurations under the framework of the present invention. For example, the cross section of the gas tube do not have to be round shape, instead, it can be square shape or other polygonal shape; the ions extracted cannot only be detected by an ion trap analyzer, but also by a quadrupole analyzer. If differentially pumped interface is used for ion extraction, other mass analyzers such as Time-of-Flight, Oribitrap, and tandem MS systems can also be used.

What is claimed is:

1. A device for separating, enriching and detecting ions, comprising:
    a gas tube for containing a gas flow having an uniform velocity;
    an ion source for producing at least one type of ions into the gas tube with the gas flow;
    a plurality of electrodes, disposed in the gas tube, and applied with a plurality of voltages, respectively, so as to form inside the gas tube at least one region having an electric field along the axis of the gas tube, such that an electric force exerting to the ions when the ions flows through the at least one region is in a direction opposite to the gas flow, whereby ions with a specific mobility are immobilized and enriched therein by the balance of its electro-drifting velocity with an axial flow velocity of the gas flow;
    an ion detector; and
    an ion extraction channel configured such that the enriched specific ions are brought out of the gas tube from its wall and led to the ion detector through the ion extraction channel.

2. The device as claimed in claim 1, wherein the electric field generated in the at least one region of the gas tube is uniform in strength along the axis of the gas tube.

3. The device as claimed in claim 2, wherein the electric field generated in the at least one region of the gas tube varies with time by varying the voltages applied to the plurality of electrodes, thereby causing ions of different mobility to be enriched in the at least one region of the gas tube at different times.

4. The device as claimed in claim 1, wherein the gas tube has multiple electric field regions formed therein by configuring the plurality of voltages applied to the plurality of electrodes, wherein the field strength within each electric field region is axially uniform, and the field strengths of the multiple electric field regions step up along the direction of the gas flow, thereby causing ions of different mobility to be immobilized and enriched in respective electric field regions.

5. The device as claimed in claim 1, wherein the plurality of voltages applied to the plurality of electrodes is configured such that the field strength of the electric field generated in the at least one region of the gas tube is gradually increased along the direction of the gas flow.

6. The device as claimed in claim 1, wherein the gas tube further has an additional region formed therein at the upstream of the at least one region, wherein the strength of the axial electric field in the additional region is gradually increased along the gas flow direction so that the field strengths at the adjacent boundaries of the additional region and the at least one region are identical.

7. The device as claimed in claim 1, wherein the electric field generated by applying the plurality of voltages to the plurality of electrodes has a radial component towards the center of the gas tube.

8. The device as claimed in claim 1, wherein the plurality of electrodes comprises multiple thin mesh electrodes that separate the gas tube into sections and each section between two mesh electrodes forms a specific electric field region corresponding to certain mobility of ions to be enriched.

9. The device as claimed in claim 8, wherein each of the multiple mesh electrodes comprises a curved mesh electrode having a concave surface positioned facing the gas flow direction.

10. The device as claimed in claim 7, wherein the plurality of voltages applied to the plurality of electrodes comprises high frequency voltages with different phases that are applied to at least certain adjacent electrodes of the plurality of electrodes so as to form a radially focusing electric field component, hereby generating an effective force to ions towards the central axis of the gas tube.

11. The device as claimed in claim 10, wherein the plurality of electrodes comprises multiple curved mesh electrodes with their convex surfaces positioned facing the gas flow direction.

12. The device as claimed in claim 1, wherein the plurality of electrodes comprises an circular electrode array disposed along the inner wall of the gas tube, wherein electrodes of the circular electrode array are applied with different voltages to form an electric field along the gas flow direction.

13. The device as claimed in claim 1, wherein the gas tube has an opening defined in its wall through which the ion extraction channel is connected for extracting the ions that are gathered in the at least one electric field region in the gas tube, and wherein the position of the opening is corresponding to the axial position of the at least one electric field region where the ions are enriched.

14. The device as claimed in claim 1, wherein the ion extraction channel penetrates the wall of the gas tube and has an opening reaching the middle part of the gas tube for extracting the enriched ion in the at least one electric field region in the gas tube.

15. The device as claimed in claim 1, wherein the ion detector comprises an array of Faraday cup detectors, each Faraday cup detector being connected to one extraction channel.

16. The device as claimed in claim 1, wherein the ion detector connected with the ion extraction channel comprises a mass analyzer.

17. The device as claimed in claim 1, wherein the ion detector connected with the ion extraction channel comprises a mass analyzer in the form of an ion trap array.

* * * * *